United States Patent [19]

Kessler

[11] 4,438,591

[45] * Mar. 27, 1984

[54] ALGAL CELL GROWTH, MODIFICATION AND HARVESTING

[75] Inventor: John O. Kessler, Tucson, Ariz.

[73] Assignee: The University of Arizona Foundation, Tucson, Ariz.

[ * ] Notice: The portion of the term of this patent subsequent to Apr. 13, 1999 has been disclaimed.

[21] Appl. No.: 347,550

[22] Filed: Feb. 10, 1982

Related U.S. Application Data

[63] Continuation-in-part of Ser. No. 118,585, Feb. 4, 1980, Pat. No. 4,324,067.

[51] Int. Cl.³ .............................................. A01G 7/00
[52] U.S. Cl. ...................................................... 47/1.4
[58] Field of Search ............................................ 47/1.4

[56] References Cited

U.S. PATENT DOCUMENTS

| | | | |
|---|---|---|---|
| 3,521,400 | 7/1970 | Ort | 47/1.4 |
| 3,645,040 | 2/1972 | Ort | 47/1.4 |
| 4,055,491 | 10/1977 | Porath-Furedi | 47/1.4 X |
| 4,087,936 | 5/1978 | Savins et al. | 47/1.4 |
| 4,320,594 | 3/1982 | Raymond | 47/1.4 |
| 4,324,067 | 4/1982 | Kessler | 47/1.4 |
| 4,341,038 | 7/1982 | Bloch et al. | 47/1.4 |

Primary Examiner—Robert E. Bagwill
Attorney, Agent, or Firm—Mason, Kolehmainen, Rathburn & Wyss

[57] ABSTRACT

The present invention relates to algal cell growth, modification and harvesting, and more particularly to systems apparatus and methods for growing, enhancing the growth of and harvesting of motile swimming microorganisms, especially unicellular algae, such as Dunaliella, which multiply by cell division.

28 Claims, 8 Drawing Figures

ALGAL CELL GROWTH, MODIFICATION AND HARVESTING

This application is a continuation-in-part of application Ser. No. 118,585, filed Feb. 4,1980, now Pat. No. 4,324,067.

In accordance with one aspect of the invention, the system is so arranged that the algal cells grown and harvested over a large area which is exposed to prevailing outdoor environmental conditions are concentrated in a relatively small environmentally controlled area where the cell growth, cell variety and cell product synthesis can be further enhanced on a manageable basis through proper feeding of the cells and proper control of the environmental conditions to which the cells are exposed. In the small environmentally controlled area the nutriment factors of light irradiation, gas and nutriment infusion, temperature and cell containing liquid turbulence, among others, may be rigidly controlled. Moreover, genetic modification agencies, such as bacteria or genetic controlling molecules may easily be supplied to the small environmentally controlled area on a controlled basis. Also, the ratio of the cell layer thickness in the harvest zone to the average depth of the cell containing liquid in the small area reservoir may easily be controlled to enhance cell production and harvesting.

In accordance with another aspect of the invention, an improved harvesting system and apparatus are provided which are capable of being used on one of the large area reservoirs to effect efficient harvesting of the cells grown in the reservoir with a minimum of capital investment in equipment and minimum operating cost. In more detail, the harvesting system comprises at least one elongated carrier of substantial width which is diposed adjacent the surface of the liquid in the reservoir and is movable relative to a harvest station in which the cell slurry is removed from the carrier. Motorized moving means are provided for producing relative movement between the one or more carriers and the harvest station. In the preferred system arrangement, both computerized and manual controls are utilized to control the functioning of the motorized moving means.

This invention relates to systems, apparatus and methods for growing, enhancing the growth of and harvesting motile swimming microorganisms, especially unicellular algae, and more particularly to the growing and harvesting of algal cells of the Dunaliella genus.

It is an object of the present invention to provide improved and highly efficient systems, apparatus and methods for growing, enhancing the growth of and non-destructively harvesting free swimming motile algal cells which multiply by cell division.

It is another object of the invention to provide improved systems, apparatus and methods of the character described which are particularly useful in the growing and harvesting of algal cells of the Dunaliella genus.

It is a further object of the invention to provide an improved system of the character indicated which is so arranged that the algal cells harvested over a large area which is exposed to prevailing outdoor environmental conditions may be concentrated in a relatively small environmentally controlled area where the cell growth, cell variety and cell product synthesis can be further enhanced on a manageable basis through proper feeding of the cells and proper control of the environmental conditions to which the cells are exposed.

According to still another object of the invention, algal cell migration from the liquid containing reservoir in which the cells are disposed to the harvest zone associated with the reservoir is dramatically improved by properly proportioning the thickness of the harvest zone to the depth of the liquid in the reservoir.

It is a still further object of the invention to provide an improved and simplified cell harvest system which may be either automatically or manually controlled to perform its assigned cell harvesting function.

The invention, both as to its organization and method of operation, together with further objects and advantages thereof, will best be understood by reference to the following specification, taken in connection with the accompanying drawings, in which.

THE GENERAL SYSTEM

Figure 1:
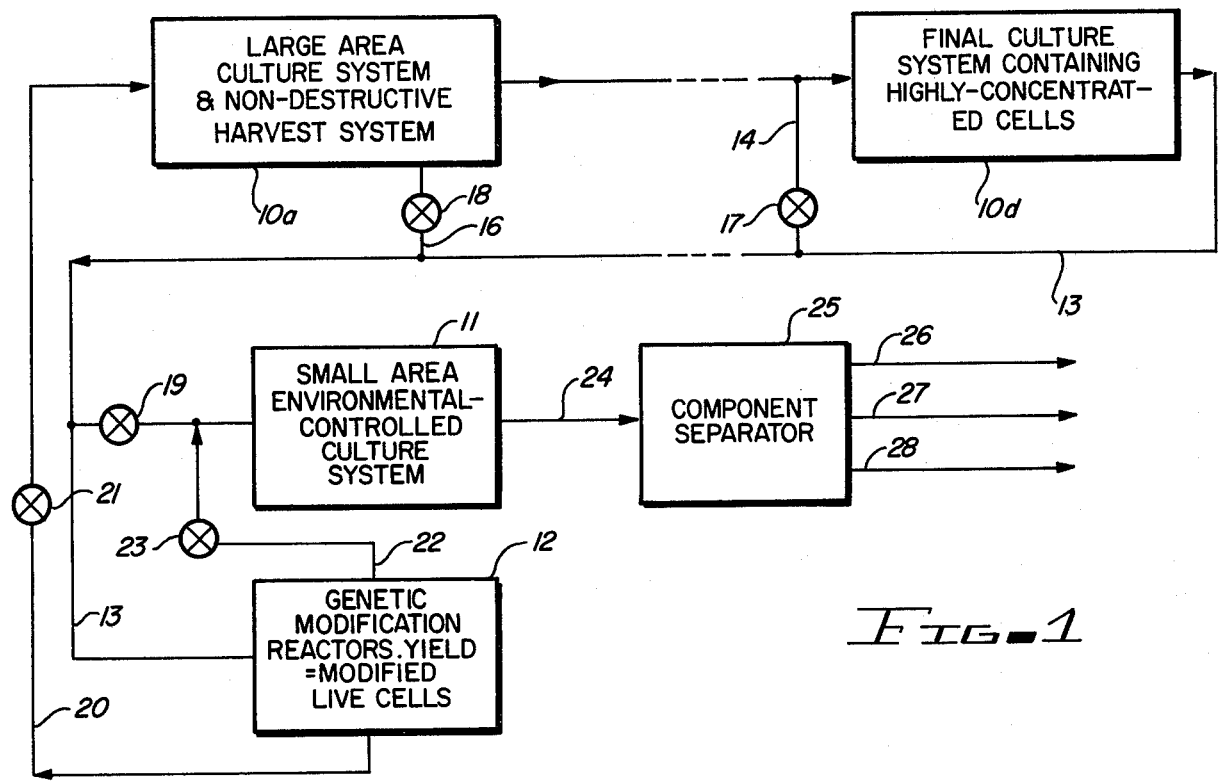
FIG. 1 is a system flow diagram illustrating the manner in which the algal cells are progressively nurtured and harvested.

Referring now to the drawings and more particularly to FIG. 1 thereof, the system there illustrated comprises a plurality of tandem related very large area algal cell growth reservoirs, the initial reservoir of which is indicated at 10a and the final reservoir of which is indicated at 10d. Cells grown and harvested in the final reservoir 10d and the intermediate reservoirs may in part be controllably delivered to each of one or more small areas of environmentally controlled reservoirs 11, genetic modification reactors 12, and back to one or more of the preceding large area reservoirs through a conduit system which comprises a plurality of connected conduits 13, 14 and 16. These conduits are appropriately valved as indicated at 17, 18, 19 and 21 to control the flow of harvested algal cells between the various stages of the system in the manner more fully explained below. Algal cells, genetically modified in the reactor 12 which includes valves not shown in the manner explained below, may be returned to the initial large area reservoir 10a through a conduit 20, which is valved as indicated at 21, or to the small area environmentally controlled reservoir 11 through a conduit 22, which is valved as indicated at 23. The harvested algal cell output from the small area environmentally controlled reservoir 11 is delivered through a conduit 24 to a component separator 25 which functions to separate the cells and the fluid which contains them, and which may also separate the cells into their various components, such as glycerol, or other hydrocarbons, lipids, proteins, water and salts. From the unit 25, the components are separately delivered to different collection or use zones through conduits 26, 27 and 28.

The specific arrangement of the large area algal cell growth reservoirs 10a-10d, as well as the cell harvesting system employed, may be as described in applicant's parent application Ser. No. 118,585, filed Feb. 4, 1980, although preferably the cell harvesting system is of the improved form illustrated in FIGS. 2, 3, 4 and 5 of the drawings and described below. Also, it has been found that the extent and rapidity of algal cell accumulation 30, see FIG. 3, on the top surface of the harvesting carrier 100, see FIG. 4, disposed adjacent the top surface of the growth liquid in the reservoir 10a, for example, as viewed in FIG. 3 of the drawings, are greatly influenced by the ratio of the thickness of the harvest zone 30a to the depth 29a of the cell growth liquid 29 in the reservoir. More specifically, the upward accumulation of cells by self locomotion from the region 29 to the region 30, as shown in FIGS. 3 and 6, proceeds at a rate approximately proportional to the concentration of cells in the lower zone of the liquid in the region 29. Defining the thickness 30a as x, the liquid depth 29a as y, the concentration of cells in the upper zone 30 as 17(t) and the starting concentration of cells in the lower zone of the liquid in the region 29 as n(o), elementary considerations show that:

$$n(t)=n(o)(y/x)(1-\exp(-vt/y)),$$

where v is the upward accumulation velocity, assumed to be independent of cell density and time in the derivation of the equation.

If the time $t=t_f$ is chosen so that the fraction of the cells which accumulate in the region 30 is f, e.g. $f=\frac{1}{2}$, the following expression is obtained:

$$n(t_f)=fn(o)(y/x)$$

The concentration of cells in the upper zone, i.e. the volume of cell material divided by the volume of growth medium, is thus increased in the upper zone, compared to the starting concentration in the lower zone by a factor $f(y/x)$. For example, if y=0.5 meter, x=0.01 meter and f=0.5, the concentration enhancement is $0.5\times0.5/0.01=25$. In practice, a factor of 6 has been observed for y=0.2 meter, x=0.03 meter and t=2 hours. These numbers yield $f=6\times.03/0.2=0.9$, which appears to be too high but can be accounted for by the cell division which takes place during the accumulation process. The increased cell concentration obtained in the upper reservoir region due to cell division is an additional benefit of maintaining the ratio of x/y as low as possible. The velocity v is generally greater than the cell swimming velocity, and it is believed that as a result of fluid convection in the region 29, which results from the hydrodynamical interaction of the cells with the growth medium in the region 29 and other causes.

The genetic modification reactor 12 performs the function of genetically modifying the algal cells fed thereto from the large area reservoirs 10a-10d through the conduit 13, to modify on a selective basis the component structures of the cells, and of returning the modified cells to the initial large area reservoir 10a through the conduit 20 and the valve 21 or to the small area environmentally controlled reservoir 11 through the conduit 22 and the valve 23. More specifically, the reactor 12 provides a controlled environment where the controlled factors include one or more of pH, dissolved salts, temperature, unusual spectral and/or intensity irradiation and specific bacterial populations, for example. The purpose of such a controlled environment is to generate, by mutation and selection of appropriate mutants, for example, through their survival, cells which are especially well adapted to the environmental conditions prevailing in the uncontrolled environment of the reservoirs 10a-10d, or which are especially useful in producing a particular desired product, such as glycerol. The reactor 12 can also be used to specifically modify the cells through their interaction with other microorganisms or as a part of an entire laboratory, operated by personnel skilled in the art of genetic modification of eukaryotic cells.

Two types of techniques appropriate to consider as embodied within the use of the system enclosed within the reactor 12 are described and further referenced in articles by Athwal and McBride, titled "Chromosome-Mediated Gene Transfer" and by M. D. Chilton, et al, titled "Characteristics of T-DNA in Crown Gall Tumors", both appearing in "Genetic Improvement Of Crops" by I. Rubenstein, et al., Editors, University of Minnesota Press, 1980. The latter article describes the method of injection of foreign DNA into eukaryotic plant cells by the prokaryotic (bacterial) plasmid Vector *Agrobacterium tumefaciens*. Cells of green algae, such as Dunaliella, are eukaryotic. Further information on this subject may be found in the article by W. J. Brill, Scientific American, 199,245, (1981), and in the book "Genetic Engineering of Osmoregulation" by D. W. Rains, et al, Plenum Press (1980). Specific information on the transformation of algal cells may be found in the article by S. Bonotto and A. Luttke, "Grafts and Transfer of Cell Constituents into the Giant Unicellular Alga *Acetabularia*," in the book "Transfer of Cell Constituents into Eukaryotic Cells," edited by J. E. Celis, et al., Plenum Press (1980).

Algal cells harvested in the small area environmentally controlled reservoir 11 are fed to the component separator 25 through the conduit 24. This separator separates the cells from the fluid medium and performs the function of breaking the algal cells down into their various chemical components, such as glycerol, other hydrocarbons, proteins, lipids, separating the components, and separately delivering the components to the output conduits such as 27 and 28. The environmental gases in the reservoir 25 may be controllably vented to atmosphere through the conduit 26 and the valve 26a. In more detail, the characteristics of the separator 25 depend upon the type of algal cell to be processed, the liquid medium in which the cells are disposed, and value judgments regarding the utility of various cell products. Since the cell concentration in the liquid entering the separator 25 is very high, fluids may be eliminated by standard methods, such as centrifugation, filtering and evaporation. The cells per se can be disrupted by osmotic or mechanical shock, as for example, by ultrasonic agitation. Standard techniques of chemical engineering separation, such as solvent extraction, chromatography, flotation, centrifugation, precipitation, or chemical reaction, may be employed to separate the cells into their separate components. These techniques are described in various text books, such as "Biomedical Engineering Fundamentals" by J. E. Bailey et al., McGraw Hill, (1977).

As will be understood from the preceding explanation, by selective manipulation of the valves 17, 18, 19, etc., varying portions of the cells harvested in the final large area reservoir 10d or in one or more of the intermediate large area reservoirs may be recycled back to a preceding large area reservoir or delivered either to the environmentally controlled small area reservoir 11 or the genetic modification reactors 12. Moreover, by selective manipulation of the valves 21 and 23, varying portions of the genetically modified cells developed within the reactor 12 may be delivered to the initial large area reservoir 10a and the small area environmentally controlled reservoir 11.

As is well understood in the art, the algal cell multiplication rate and the chemical composition of algal cells, particularly cells of the Dunaliella genus, are very heavily dependent upon the environmental conditions to which the cells are exposed and upon the nutriments which are delivered, either naturally or artificially, to the cell growth or multiplication zones. Thus, it is well known that the lipid content of green algal cells, a category which includes Dunaliella and other algae, is substantially enhanced when the cells are grown in a nitrogen starved environment. Furthermore, the character of the lipids produced, e.g. degree of saturation, and of other cellular products can be modified by the temperature and illumination prevalent in the cell growth medium. These behavioral characteristics of the cells are described in the book "Algae Biomass", G. Shelef et al., Elsevier (1980), especially in the articles by Aaronson et al, Materassi et al and Shifrin et al appearing in this book. In general cell growth or multiplication is enhanced by feeding the cells adequate amounts of carbon dioxide, by providing appropriately sequenced illumination of an intensity suitable for the particular cell species, and by inducing a mixing turbulence of the liquid, for example saline water, in which the cells are disposed. These ends are artificially achieved through provision of the small area environmentally controlled reservoir 11 in the system.

Figure 7:
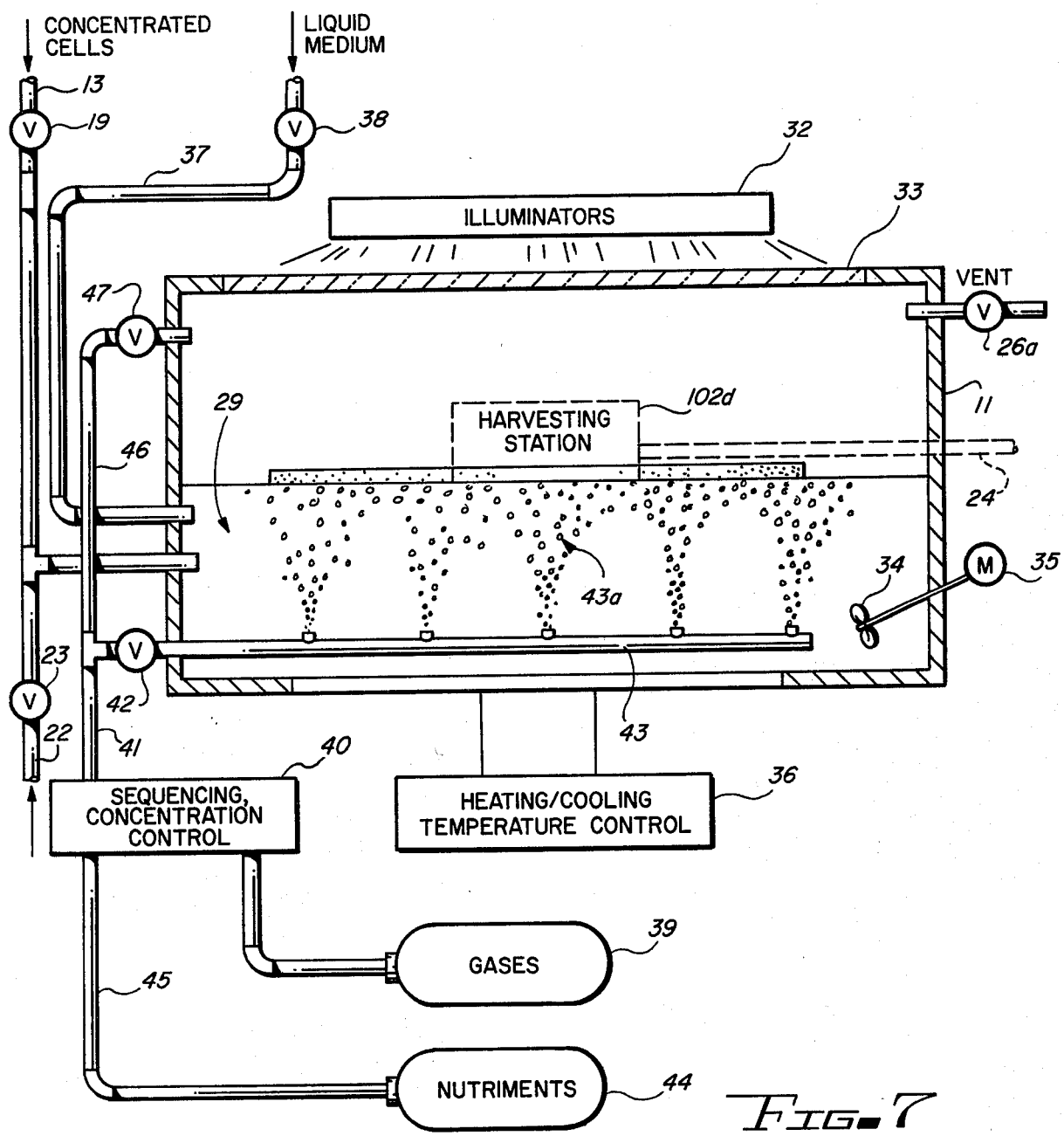
FIG. 7 is a view, partially in section, illustrating certain details of the environmentally controlled reservoir forming a part of the system illustrated in FIG. 1.

As best shown in FIG. 7 of the drawings, the small area environmentally controlled reservoir 11 is in the form of a closed chamber which is not exposed to prevailing outdoor environmental conditions, but on the contrary, has a controlled atmosphere therewithin. This chamber although illustrated as a relatively small closed container will in practice have a substantial bottom surface area and small volume, and may consist of a number of similar replicates connected in tandem. It serves to contain the liquid cell containing growth medium 30, derived from the harvest station associated with one of the large scale reservoirs 10a–10d. Since the volume of the reservoir 11 is much smaller than the volume of each of the reservoirs, by a factor of the order of 1 to 1000, these cells may be easily and economically extracted from the reservoir 11, as indicated at 102d, by standard means such as flotation, filtration or centrifugation. It should be noted that whereas it is important that the cells be alive when introduced into the reservoir 11, so that they may modify their constitution within the controlled environment of this reservoir, it is not necessary to deliver live cells to the separator 25. For that reason, it is important that the harvest systems employed in the reservoirs 10a–10d be non-destructive, but it is unimportant that live cells be delivered from the reservoir 11 to the separator 25.

For the purpose of controlling the environmental conditions within the reservoir 11, special illuminators or light sources, liquid agitating means and liquid medium temperature control means are provided. The illuminators may take the form of elongated electrically energized light tubes 32 which emit light of particular selected wave lengths and intensity and are positioned above light transparent cover plates 33 that serve to close the top of the reservoir 11 and to permit light from the light tubes 32 to impinge upon the algal cells and upon the liquid growth medium in the reservoir 11. Agitation of the liquid 29 in the reservoir 11 is provided by gas bubbles 43a and by an agitating propeller 34 which is adapted to be driven at a relatively slow speed by an adjustable speed electric motor 35. The optimum temperature for maximum cell growth or multiplication or cell content modification is maintained within the reservoir 11 by means of conventional heating and cooling apparatus schematically indicated as a heating and cooling unit 36. Cell growth liquid medium, e.g., saline water of the proper salinity, may be supplied to the reservoir 11 from time to time as required from an appropriate source, not shown, through a conduit 37 which is valved as indicated at 38 to enable the liquid flow therethrough to be turned on and off.

Treating gases, such for example as carbon dioxide, hydrogen, ammonia, air, sulfur dioxide, argon, etc., which serve to optimize algal cell modifications within the reservoir 11, are adapted to be supplied to the cell growth liquid 29 in the reservoir 11 from a pressurized source 39 through a sequencing and concentration control device 40 and a conduit 41 which is valved as indicated at 42. The output side of the valve 42 is connected to a bubbler 43 positioned adjacent the bottom of the reservoir and adapted to release gas derived from the source into the cell growth liquid 29 at spaced intervals along the bubbler 43. Buffers and nutriments, such, for example, as ammonium sulfate and potassium sulfate, solutions may be delivered to the upper gas filled portion of the reservoir from a nutriment source 44 which is conduit connected through the sequencing and concentration control device 40 by means of conduits 45 and 46 and the conduit 41, the conduit 46 being valved as indicated at 47 to control the delivery of nutriments from the source 44 to the interior of the reservoir 11. As will be understood, the nutriments in the source 44 are of liquid or semi-liquid consituency and are delivered to the reservoir 11 through the conduits 45, 41 and 46 as required by gaseously pressurizing the source 44. Genetically modified algal cells may selectively be delivered to the reservoir 25 from the reactors 12 through the conduit 22 and the valve 23.

The sequencing concentration control device 40 performs the function of supplying the appropriate physicochemical environment to the algal cells. For example, it may intermittently provide nutriments or nitrogens to synchronize cell division in the entire cell culture and then provide at intermittent intervals, appropriately phased with respect to culture synchrony, other chemicals, e.g., enzymes, which most efficiently stimulate the production of desired cell synthates during a specific phase of the cell cycle. The timing of the sequencing control device 40 must be integrated into intermittencies introduced into the other controlled environmental factors, such as temperature, illumination, salinity and pH. The influence of cell synchrony on algal cell productivity is discussed by Lorenzen in Shelef et al., cited infra.

As will be understood from the preceding explanation, the small area reservoir 11 is completely environmentally controlled to produce optimum conditions for the growth, multiplication or modification of the content or products of the algal cells disposed in the liquid growth medium 29 contained within this reservoir. Thus, by selective manipulation of the valves 19 and 38 the relative amounts of cell slurry and liquid growth medium supplied to the reservoir 11 may easily be controlled as desired. Moreover, by manipulation of the valve 23, genetically modified algal cells may be delivered to the reservoir 11 from the reactors 12 from time to time as required to maintain the desired cell species situated within the reservoir 11. Through conventional control of the illuminators 32, light of the proper intensity and wave length is delivered to the algal cells disposed within the reservoir 11. The desired turbulence of the cell growth liquid 29 within the reservoir 11 is established by controlling the operating speed of the motor 35 which drives the agitating propeller 34. Finally, gases, such as carbon dioxide, derived from one or more sources 39, or nutriments derived from one or more sources 44, may be delivered to the reservoir 11 through selective manipulation of the valves 42 and 47 and operation of the device 40.

Thus, by limiting the volume and the surface area of the growth medium 29 within the chamber 11, it is possible to establish a cell growth environment and cell species controls which from a practical standpoint are not possible to attain in the large area reservoirs 10a–10d. In this context, it is pointed out that the surface area of each of the reservoirs 10a–10d may cover a large acreage which makes it totally impractical to attempt artificially to control the environmental conditions prevailing in, over and around each of these reservoirs. For example, the surface area $a^2$ within the small area reservoir 11, assumed to be cubical and of liquid containing volume $a^3$ can be compared with the sum of the surface areas A of the reservoirs 10a–10d, from which an algal slurry, having an average depth x, denoted by 30a, in FIG. 3, has been harvested and conduited into the reservoir 11. The area ratio $A/a^2$ is 1000, assuming A=10ha, i.e. 100,000 meters$^2$ or somewhat more than 20 acres, such that x=0.01 meter. The volume $a^3 = A \times 10^3 = 10^3$ meters$^3$. Assuming the slurry has a cell concentration of $5 \times 10^7$ cells /ML, and assuming further that the algae are Dunaliella stimulated to produce glycerol within the reservoir 11, the glycerol production from one filling of the reservoir 11 is approximately 2 to 17 tons, depending upon cell size.

THE HARVESTING SYSTEM

Figure 2:
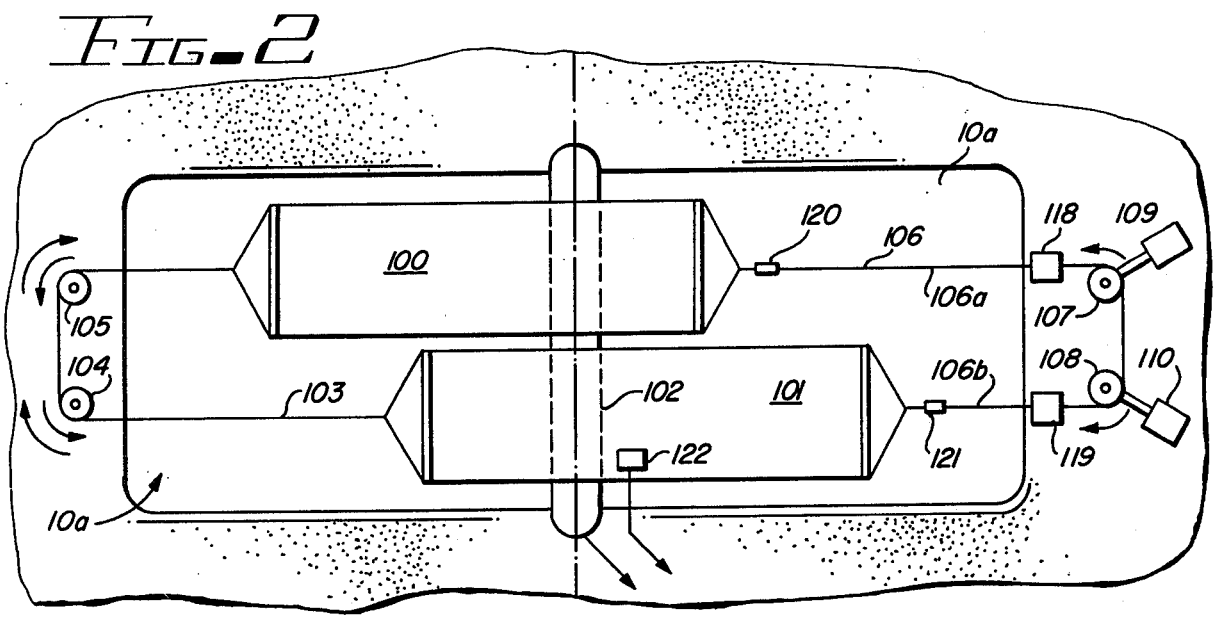
FIG. 2 is a top plan view of the improved cell harvesting arrangement embodied in the system of FIG. 1 at various stages thereof.
Figure 3:
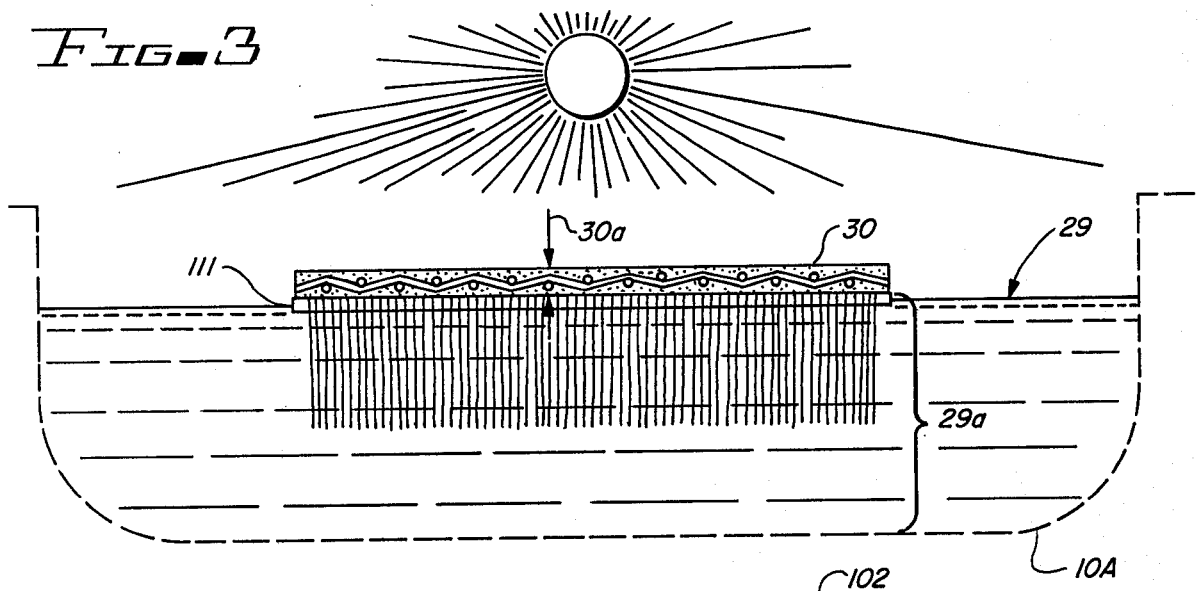
FIG. 3 is a partial sectional view of one of the components embodied in the cell harvesting system shown in FIG. 2.

Referring now more particularly to the present improved cell harvesting system, as illustrated in FIG. 2 of the drawings, this system comprises a pair of elongated carriers 100 and 101 which are arranged in side-by-side relationship adjacent the surface of the liquid in the reservoir 10a, for example, and are adapted to be slowly moved back and forth in opposite directions across the reservoir relative to the stationary cell harvest station 102. At their left ends as viewed in FIG. 2 of the drawings, the carriers are connected by a cable 103 which passes around a pair of idler rollers 104 and 105. These rollers serve to maintain the desired lateral spacing between the left end portions of the carriers 100 and 101. At their right ends, as viewed in FIG. 2 of the drawings, the carriers are connected by means of a second cable 106 which passes around a pair of capstan drive rollers 107 and 108, suitably spaced apart to maintain the desired lateral spacing between the right end portions of the carriers. Adjustable speed drive motors 109 and 110 are provided which are shaft connected to the capstan drive rollers 107 and 108, respectively, and are adapted to drive these rollers at controlled varying speeds in opposite directions.

Preferably the carriers 100 and 101 are formed of a light weight mesh material which serves to support the discrete elements e.g. cotton fibers, of the cell migration mass in the manner shown in FIG. 3 of the drawings. These composite carrier and fiber structures are preferably capable of floating on or near the surface of the liquid in the reservoir 10a. In order to enhance the floating capabilities of the carriers 100 and 101 float bars 111 are provided which are attached at spaced intervals along the lengths of the carriers and extend transversely thereof in the manner shown in FIG. 4 of the drawings, and the cables 103 and 106 are tensioned around the rollers 104, 105, 107 and 108 to maintain the carriers 100 and 101 elongated and under tension.

Figure 4:
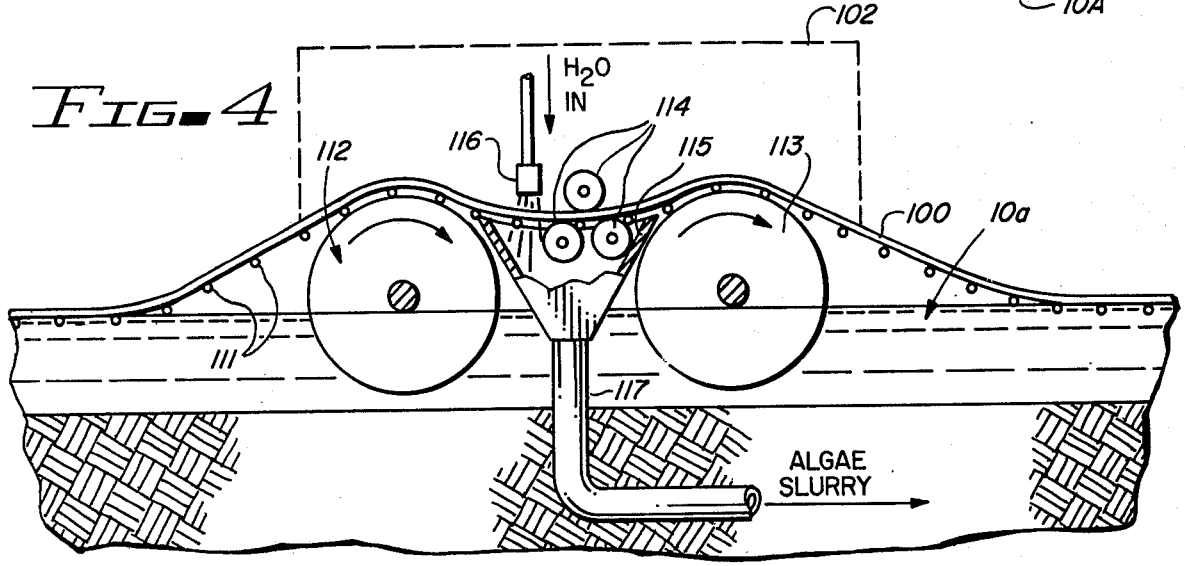
FIG. 4 is a fragmentary sectional view illustrating further components of the cell harvesting system of FIG. 2.

For the purpose of harvesting the algal cells from the top surfaces of the carriers 100 and 101, the harvest station 102 is provided, the details of which are illustrated in FIG. 4 of the drawings. As there shown, within the harvest station 102, each of the carriers 100 and 101 is passed over a pair of relatively large diameter and spaced apart idler rollers 112 and 113 which serve to lift the traveling segments of the carriers well above the surface of the liquid in the reservoir 10a. Between the idler rollers 112 and 113, the carriers pass between freely rotatable squeeze rollers 114 which are positioned above the large mouth of a cell collection funnel 115. In order to dislodge the cells from the surfaces of the carriers 100 and 101, pressurized spray nozzles 116 are provided to which are delivered pressurized liquid derived partly from the reservoir 10a and partly from the cell slurry delivered from the funnel 115. The algal slurry thus collected in the funnel 115 is delivered to the next succeeding large area reservoir in the tandem related reservoir system or to the reservoir 11 through a conduit 117.

A modified and somewhat simpler harvest station arrangement is illustrated in FIG. 6 of the drawings. In this modified arrangement, algal cell slurry is adapted to be removed from the harvest zone on top of the carriers 100 and 101, or preferably from the fluid harvest zone 30 situated over a stationary harvest material of fibrous or porous nature, located below the surface of the reservoir fluid 29, by means of a suction conduit 8. Any suitable suction producing device may be operatively associated with the conduit 8 for producing suction at the downwardly faced orifices in the nozzle 9.

Figure 8:
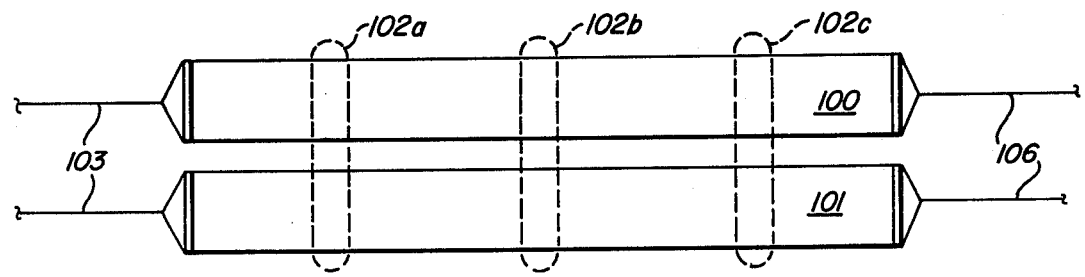
FIG. 8 illustrates a modified arrangement of the harvest system.

In order to shorten the length of travel of the carriers 100 and 101 back and forth across the surface of the liquid in the reservoir 10a and at the same time harvest all of the cells which migrate to the top surfaces of these carriers, the multi-harvest station arrangement illustrated in FIG. 8 may be employed. As there shown, a plurality of evenly spaced harvest stations 102a, 102b and 102c may be provided along the top surfaces of the reservoir 10a, each of which may be of the component arrangement illustrated in FIG. 4 of the drawings and described above. By employing the spaced three harvest station arrangement, the length of travel back and forth across the surface of the liquid in the reservoir 10a is shortened to approximately one half of that required with the single harvest system arrangement illustrated in FIG. 2 of the drawings.

For the purpose of controlling the operation of the motors 109 and 110 to effect back and forth movement of the carriers 100 and 101 across the surface of the reservoir 10a, control means of the form diagramatically illustrated in FIG. 5 of the drawings, operating in cooperation with the sensing elements associated with the carriers and described immediately below, may be employed. These sensing elements comprise a pair of stationary micro-switches 118 and 119 positioned adjacent and immediately above the segments 106a and 106b of the cable 106 and adapted to be actuated from normally open circuit settings to closed circuit settings by enlarged actuating bumpers 120 and 121 respectively, which are carried by and fixedly attached to the cable segments 106a and 106b. A stationary algal cell concentration sensing device 122 is also provided which is positioned adjacent to and above the carrier 101 and functions to measure the extent of algal cell concentration on the top surface of the carrier. This cell concentration detector may be of any desired type, such, for example, as an optical system which measures the shading effect of the algal cells as they accumulate on top of the carrier 101 or a color responsive optical system which senses the color change, e.g., to green, resulting from algal cell accumulation on the top surface of the carrier 101.

Figure 5:
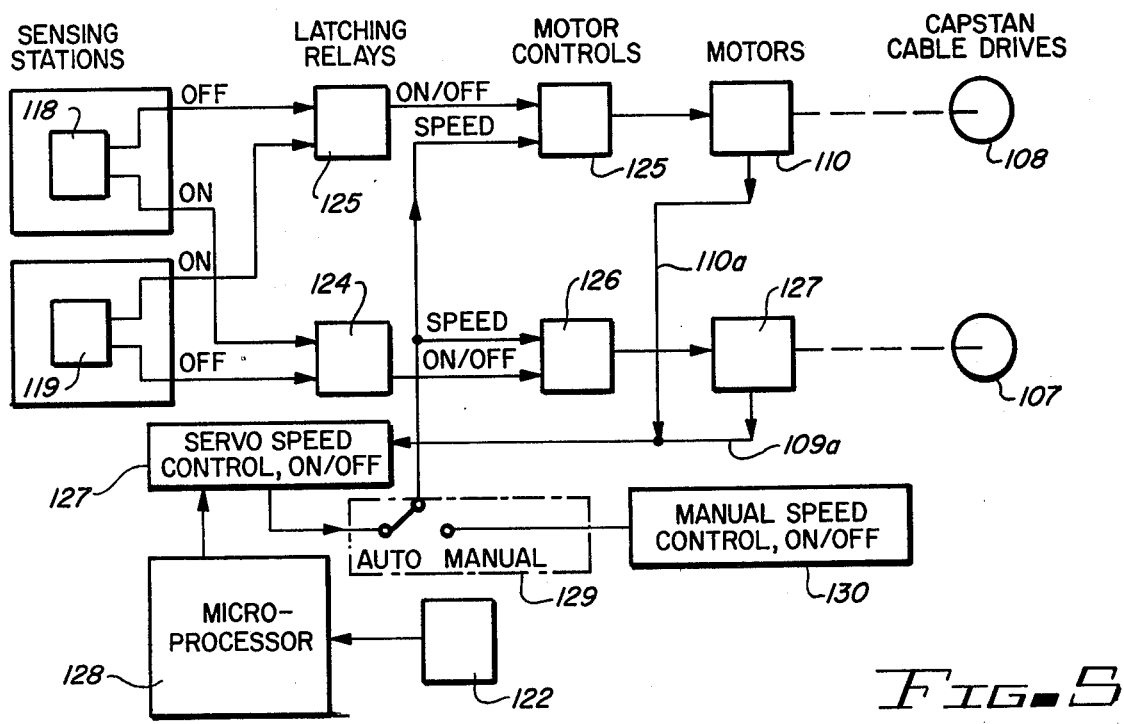
FIG. 5 is a block diagram of the control system which may be utilized to control the operation of the harvesting system shown in FIG. 2.
Figure 6:
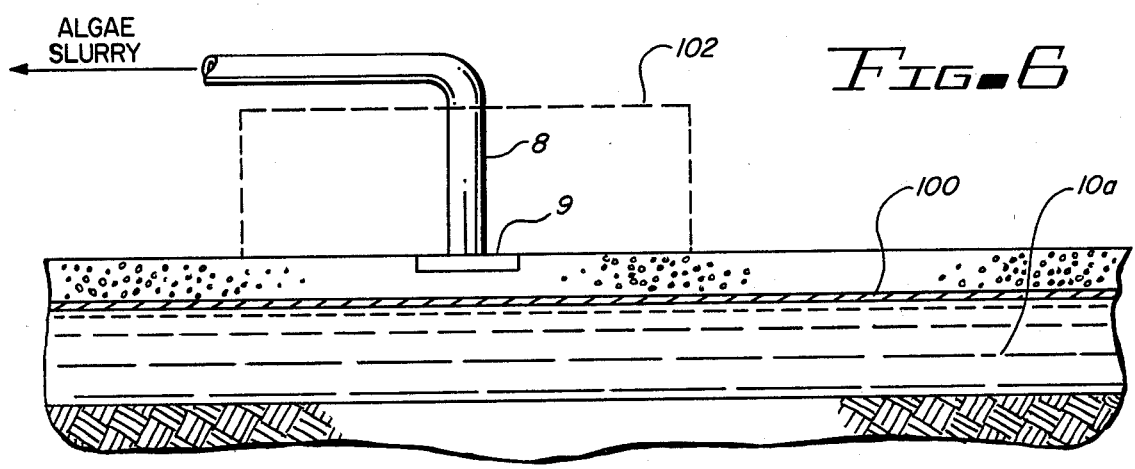
FIG. 6 is a view illustrating modified apparatus for removing algal cells from the traveling carriers forming part of the cell harvesting apparatus shown in FIG. 2.

As shown in FIG. 5 of the drawings, the position sensing micro-switches 118 and 119 and the cell concentration detector 122 cooperate with the other components of the control network to control the starting and stopping of the drive motors 109 and 110 and the operating speeds thereof. More specifically, the carrier position sensing micro-switches 118 and 119 directly control bi-stable latching relays 123 and 124 which in turn control the motor "on" and "off" directives imposed upon motor control networks 125 and 126. A servo network 127, controlled in part by a microprocessor computer 128, serves in part to control the motor control units 125 and 126 and hence the drive motors 109 and 110. The computer 128 is directly controlled by the cell concentration detector 122 and if desired may be used to perform a variety of other functions such, for example, as controlling the salinity of the liquid in the associated cell growth reservoir, and other physical factors associated with highly efficient operation of the overall system. If desired, control of the motor control units 125 and 126 by the computer 128 and the servo network 127 may be manually overridden through operation of the override switch 129 and manual operation of the manual on-off and speed control unit 130.

OPERATION OF THE HARVEST SYSTEM

As will be understood from the preceding explanation, normally the carriers 100 and 101 remain stationary, or move very slowly, in order to permit algal cells to build up on the top surfaces of the carriers in the manner fully explained in applicant's copending application Ser. No. 118,585, filed Feb. 4, 1980. When a predetermined cell concentration or density is achieved on the tops of the carriers 100 and 101, the cell concentration detector 122 signals the micro-processor 128 that movement of the carriers relative to the harvest station 102 should be initiated or accelerated, with the result that one of the two motors 109 or 110 is energized to start back and forth movement of the carriers. Alternatively, the degree of cell concentration on the carrier tops can be visually determined and the above described manual controls can be utilized to initiate operation of one of the two motors 109 and 110.

Assuming that the motor 109 is energized, the capstan drive roller 107 functions to drive the closed loop comprising the connector components 100, 103, 101 and 106 in a counterclockwise direction as viewed in FIG. 2, with the result that the carrier 100 is moved to the left and the carrier 101 is moved to the right past the harvest station 102. As the travel limits of the two carriers are reached, the camming bumper 121 operates the microswitch 119 to signal the control system of FIG. 5 to deenergize the motor 104 and thus arrest the movement of the carriers. The carriers 100 and 101 remain stationary pending a second build up of algal cell slurry on the tops thereof. When a predetermined cell concentration is attained, the detector 122 again signals the control system of FIG. 5 that movement of the carriers should again be initiated. In this case, the control system operates to energize the motor 110 which, through its associated capstan drive roller 108, functions to drive the closed loop comprising the connected components 100, 103, 101 and 106 in a clockwise direction as viewed in FIG. 2. As a consequence, the carrier 100 is moved to the right and the carrier 101 is moved to the left as viewed in FIG. 2, with both carriers traversing the stationary harvest station 102. Such carrier movement continues until the camming bumper 120 engages and operates the microswitch 118 which signals the control system of FIG. 5 and more particularly the microprocessor to stop the carrier movement. As a result, the motor 110 is deenergized to arrest movement of the carriers and the harvest system remains quiescent or in a state of very slow movement, as described below, pending another algal cell slurry build-up on the tops of the carriers.

As will be understood from the above explanation, the carriers 100 and 101 are intermittently moved back and forth across the surface of the reservoir 10a in response to a predetermined and repetitive algal cell slurry build-up on the top surfaces of the carriers. As the carriers 100 and 101 pass through the harvest station 102 the algal slurry is removed from the top surface harvest zones thereof and delivered to the outlet conduit 117, shown in FIG. 4. More specifically, as the travelling carrier 100, for example, passes through the harvest station 102, it is lifted by the rollers 112 and 113, squeezed by the squeeze rollers 114 and passed beneath the spray nozzle, or nozzles, 116. As a consequence, the algal cell slurry is squeezed out of the carrier 100 and washed off the top surface of the carrier and falls into the large mouth of the funnel 115 for delivery to a succeeding stage of the system through the conduit 117. As explained above, the liquid delivered to the spray nozzles 116 is partially derived from the reservoir 10a and partially from the slurry output in order to minimize dilution of the latter. Any suitable pump means may be utilized for pumping liquid from the reservoir 10a and the conduit 117 and delivering the same under pressure to the nozzle 116.

As indicated above, it may prove to be desirable under certain circumstances to operate the carriers 100 and 101 in very slow but continuous back and forth motion and to achieve harvesting intermittently under the control of the micro-processor 128 and the sensor 122. This can be accomplished by utilizing the microprocessor 128, as controlled by the sensor 122, intermittently to turn the spray nozzle on and off at spaced intervals determined by the degree of cell concentration on the carriers 100 and 101. This form of operation serves to enhance the detection efficiency of the sensor 122 and enhances the illumination and mixing of the algae containing liquid below the carriers 100 and 101.

If the suction form of algal cell removal means illustrated in FIG. 6 of the drawings is employed in the harvest station 102, it is not necessary to elevate the carrier 100, for example, above the surface of the liquid in the reservoir 10a during the cell harvesting operation in the manner just described. Specifically, the suction nozzle 9 carried at the end of the suction conduit 8 is located below and in close proximity to the top surface of the slurry on the carrier 100 and spans the width of this carrier. Suction means, not shown but of any conventional design, are connected to the conduit 8 to produce a very low subatmospheric pressure at the input orifices of the nozzle 9. As a consequence, the algal slurry accumulation on the top of the carrier 100 is sucked up from around the region of the nozzle 9 as the carrier travels beneath this carrier and is delivered through the conduit 8 to a succeeding stage of the system.

Referring now more particularly to the operation of the control system diagramatically illustrated in FIG. 5 of the drawings, it will be understood from the above explanation that this system receives stop signals from the microswitches 118 and 119 when the carriers 100 and 101 respectively reach their terminal positions to the right as viewed in FIG. 2 of the drawings. The control system also receives a start signal from the cell concentration detector 122 when the algal cell concentration on top of the carrier 101, for example, reaches a predetermined level and a stop signal from this detector when the algal cells are removed from the carrier 101 in the harvest station 102 in the manner explained above. Depending upon the design of the detector 122, it may also function to measure and deliver appropriate signals to the control system when the algal cell density or concentration on top of the carrier reaches a plurality of predetermined different levels.

As explained above, when the sensing station, i.e., the micro-switch 118, is operated by the camming bumper 120, it delivers an OFF signal to the latching relay 123 and an ON signal to the latching relay 124. The OFF signal delivered to the latching relay 123 causes this relay to operate from one of its two stable settings to the other and in so doing to open-circuit the motor solenoid embodied in the motor control unit 125. As a consequence, operation of the motor 110 is arrested. The ON signal delivered to the latching relay 124 causes this relay to shift to its bi-stable motor-start setting, thus causing the motor-start solenoid in the motor control unit 126 to operate and initiate operation of the motor 109, thereby to drive the carriers 100 and 101 in the reverse direction. When the terminal position of the carrier 101 is reached, the camming bumper 121 operates the micro-switch of the sensing station 119, causing this station to deliver an OFF signal to the latching relay 124 and an ON signal to the latching relay 123. As a result, the motor control unit 126 operates to arrest the operation of the motor 109 and the motor control unit 125 is operated to restart the operation of the motor 110.

The described alternate operation of the drive motors 109 and 110 continues until the operation of both motors is arrested under the control of the micro-processor 128 and the cell concentration detector 122. In more detail, when the algal slurry concentration in the harvest zone of the carrier 101 is reduced below a certain predetermined level through operation of the harvest station 102, the cell concentration detector 122 signals the micro-processor 128 to that effect. As a consequence, the micro-processor, operating in conjunction with the servo speed control and motor ON-OFF unit 127 delivers motor stop signals through the switch 129 to each of the motor control units 125 and 126. These motor control units respond to the motor stop signals by immediately deenergizing whichever motor 109 or 110 is operating, thereby to arrest the movement of the carriers 100 and 101 regardless of the positions which these carriers occupy.

When the algal cell concentration level in the harvest zone atop the carrier 101 again builds up to a predetermined level, the cell concentration detector 122 signals the micro-processor 128 to that effect, with the result that the micro-processor 128, acting in conjunction with the servo unit 127 delivers a motor start signal to the motor control unit 125 or 126 which is conditioned to effect resumed operation of its associated motor 109 or 110 in the manner explained above. One of the functions performed by the unit 127 is that of controlling the operating speeds of the motors 109 and to hold the same constant at the speed level dictated by the micro-processor 128. To this end, servo loops comprising the cables 109a and 110a are provided for feeding back to the unit 127 signals indicative of the actual operating speeds of the motors 109 and 110.

Normally, the operating speed of each of the motors 109 and 110 is set at a predetermined constant speed level within the micro-processor 128 and the servo speed control and ON-OFF control unit 127. However, if the cell concentration detector 122 is designed to produce a changing signal representative of different degrees of cell concentration in the harvest zone of the carrier 101, the micro-processor 128 and control unit may be designed to respond to this changing signal by altering the operating speed of the particular motor 109 or 110 which is in operation. In general, the two units 128 and 127 will respond to the changing signal delivered by the detector 122 by slowing the operating speed of the activated motor 109 or 110 when the cell concentration of the harvest zone on the carrier 101 is light and by increasing the motor operating speed when the cell concentration of this harvest zone is heavy. It will be understood that with this arrangement, the motors 109 and 110 may be operated continuously to move the carriers 100 and 101 back and forth across the liquid surface of the reservoir 10a.

If desired or required in an emergency situation, operation of the automatic control system just described may be overridden and manual control substituted therefor. To this end, the switch 129 is operated from its AUTO setting to its MANUAL setting to deactivate the automatic control system described above and place the control of the motor control units 125 and 126 under the control of the manual speed control ON-OFF network 130. With the switch 129 in its MANUAL setting, the various controls of the unit 130 may be selectively operated to effect selective operation of one of the motors 109 and 110, but not both at the same time, and the speed control components of the unit 130 may be selectively actuated to control the operating speed of the particular motor which is in operation.

While the best mode of practicing the invention has been described, it will be understood that various modifications may be made in the disclosed system, methods and apparatus without departing from the true spirit and scope of the invention as defined in the appended claims.

What is claimed and desired to be secured by Letters Patent of the United States is:

1. A system for growing, enhancing the growth of and harvesting algal cells which multiply by cell division, comprising at least one relatively large area cell growth liquid containing reservoir in which said cells are initially disposed for multiplication by cell division, said reservoir being exposed to prevailing outdoor environmental conditions and being provided with a concentrated cell harvest zone adjacent the top surface of the liquid contained therein, cell migration means for effecting self-locomoted migration of the cells in said reservoir to said harvest zone, a relatively small area cell growth liquid containing reservoir, transfer means for transferring concentrated cells from said harvest zone to said small area cell growth liquid containing reservoir, and environmental control means for controlling the environmental conditions to which the cells in said small area liquid containing reservoir are exposed.

2. A system as claimed in claim 1, wherein the surface area of the liquid in said large area reservoir exceeds the surface area of the liquid in said small area reservoir by a factor of the order of 1000 to 1 when the large area reservoir is 100,000 meters$^2$ in size or larger.

3. A system as claimed in claim 1 or claim 2, wherein the thickness of said harvest zone is less than 1/10 (one tenth) the average depth of the liquid in said small area reservoir.

4. A system as claimed in claim 1, wherein said harvest zone comprises at least one elongated carrier which supports said cell migration means, and means are provided for moving said carrier back and forth across the surface of the liquid in said large area reservoir.

5. A system as claimed in claim 1, wherein said environmental control means includes apparatus for controlling one or more of the factors of light intensity and spectrum, liquid turbulence, nutriment supply and the temperature to which said cells are exposed in said small area reservoir.

6. A system as claimed in claim 1 or claim 5, wherein said small area reservoir comprises a closed chamber which is not exposed to surrounding environmental conditions.

7. A system for growing algal cells which multiply by cell division, comprising a liquid containing reservoir in which said cells are disposed for multiplication by cell division, a cell harvest zone located adjacent the top surface of the liquid in said reservoir and cell migration means for effecting self-locomoted cell migration of the cells in said reservoir to said harvest zone, the thickness of said harvest zone being less than 1/10 I(one tenth) the average depth of the liquid in said reservoir.

8. A system as claimed in claim 1, wherein said harvest zone comprises at least one elongated carrier, one part of said carrier comprising a material mass which provides a migration path for self-locomoted migration of said cells and which retains the cells which have migrated from said reservoir through said mass in the vicinity of the top of said carrier, and wherein a cell harvest station is provided adjacent the top surface of said carrier, and moving means are provided for producing relative movement between said carrier and said harvest station.

9. A system as claimed in claim 8, wherein said harvest station is stationary and said moving means is operative to move said carrier back and forth across the top surface of the liquid in said large area reservoir.

10. Apparatus for harvesting algal cells from a liquid containing reservoir in which said cells are disposed for multiplication by cell division, comprising an elongated carrier disposed adjacent the surface of the liquid in said reservoir, a material mass supported by said carrier and at least partially disposed in the liquid in said reservoir to provide a migration path which enables cells in said liquid to migrate by self-locomotion from the liquid in said reservoir through said mass to a harvest zone located adjacent the top of said carrier, a cell harvest station disposed adjacent the top of said carrier and including means for removing cells from said carrier during relative movement between said carrier and said station, and drive means for producing relative movement between said station and said carrier.

11. Apparatus as claimed in claim 10, wherein said harvest station is stationary and said drive means is operative to move said carrier back and forth across the top surface of the liquid to reservoir.

12. Apparatus as claimed in claim 10, wherein control means for monitoring the degree of cell concentration on the top of said carrier are provided for controlling the operation of said drive means.

13. Apparatus as claimed in claim 10, wherein said harvest station comprises means for effecting spray removal of said cells from said carrier.

14. Apparatus as claimed in claim 10, wherein said harvest station comprises means for spraying liquid onto said carrier, thereby to effect spray removal of said cells from said carrier.

15. Apparatus as claimed in claim 10, wherein said harvest station comprises means for spraying cell containing slurry at least partially derived from the output side of said harvest station onto said carrier, thereby to effect spray removal of said cells from said carrier.

16. Apparatus as claimed in claim 10, wherein said harvest station comprises means for spraying cell containing liquid at least partially derived from said reservoir onto said carrier, thereby to effect spray removal of said cells from said carrier.

17. Apparatus as claimed in claim 10, wherein said harvest station comprises means for spraying cell containing liquid partially derived from said reservoir and partially derived from the output side of said harvest station onto said carrier, thereby to effect spray removal of said cells from said carrier.

18. Apparatus as claimed in claim 10, wherein said harvest station comprises spray means for effecting spray removal of said cells from said carrier, and collecting means disposed beneath said spray means for collecting the cells removed from said carrier.

19. Apparatus as claimed in claim 10, wherein said harvest station comprises spray means for spraying cell containing liquid at least partially derived from said reservoir onto said carrier thereby to effect spray removal of said cells from said carrier, and collecting means disposed beneath said spray means for collecting the cells removed from said carrier.

20. Apparatus as claimed in claim 10, wherein said harvest station includes suction means for effecting suction removal of cells from said carrier.

21. Apparatus as claimed in claim 10, wherein said drive means comprises at least one motor, and means are provided for controlling the operation of said motor in accordance with the degree of cell concentration on said carrier.

22. Apparatus for harvesting algal cells from a liquid containing reservoir in which said cells are disposed for multiplication by cell division, comprising a pair of elongated carriers disposed in side-by-side relationship adjacent the surface of the liquid in said reservoir, a material mass supported by each of said carriers and at least partially disposed in the liquid in said reservoir to provide migration paths which enable cells in said liquid to migrate by self-locomotion from the liquid in said reservoir through said masses to the tops of said carriers, a cell harvest station disposed adjacent and spanning the tops of said carriers and including means for removing cells from said carriers during relative movement between said carriers and said station, and drive means for simultaneously moving said carriers in opposite directions back and forth relative to said harvest station.

23. Apparatus as claimed in claim 22, wherein control means are provided for controlling said drive means to start and stop movement of said carriers and to control the speed of relative movement between said harvest station and said carriers.

24. Apparatus as claimed in claim 23, wherein said control means includes means for sensing the degree of cell concentration on said carriers.

25. The method of growing, enhancing the growth of and harvesting algal cells which multiply by cell division, comprising initially growing said cells in a relatively large area cell growth liquid containing reservoir in which said cells are initially disposed for multiplication by cell division, said reservoir being exposed to prevailing outdoor environmental conditions, contacting a surface of the liquid in said reservoir with a cell carrier for a time sufficient to permit a portion of the cells to migrate into said cell carrier, removing a portion of the cells from said cell carrier, transferring cells removed from said cell carrier to a relatively small area cell growth liquid containing reservoir, supplying cell metabolism modifying substances to the cells transferred to said small area reservoir, artificially controlling the environmental conditions to which the cells in said small area liquid containing reservoir are exposed, and harvesting at least a portion of the cells grown in said small area liquid containing reservoir.

26. The method as claimed in claim 25, wherein the surface area of the liquid in said large area reservoir exceeds the surface area of the liquid in said small area reservoir by a factor of the order of 1000 to 1 when the large area reservoir is at least 100,000 meters$^2$ in size.

27. The method as claimed in either claim 25 or claim 26, wherein said algal cells are of the Dunaliella genus.

28. The method as claimed in either claim 25 or claim 26, wherein the liquid contained in each of said reservoirs is saline water.

* * * * *